United States Patent
Lübbert

(10) Patent No.: US 11,642,411 B2
(45) Date of Patent: May 9, 2023

(54) PHOTODYNAMIC THERAPY COMPRISING TWO LIGHT EXPOSURES AT DIFFERENT WAVELENGTHS

(71) Applicant: BIOFRONTERA BIOSCIENCE GMBH, Leverkusen (DE)

(72) Inventor: Hermann Lübbert, Leverkusen (DE)

(73) Assignee: BIOFRONTERA BIOSCIENCE GMBH, Leverkusen (DE)

( * ) Notice: Subject to any disclaimer, the term of this patent is extended or adjusted under 35 U.S.C. 154(b) by 243 days.

(21) Appl. No.: 17/269,816

(22) PCT Filed: Aug. 23, 2018

(86) PCT No.: PCT/EP2018/072823
§ 371 (c)(1),
(2) Date: Feb. 19, 2021

(87) PCT Pub. No.: WO2020/038583
PCT Pub. Date: Feb. 27, 2020

(65) Prior Publication Data
US 2021/0315993 A1    Oct. 14, 2021

(51) Int. Cl.
*A61N 5/06*     (2006.01)
*A61K 41/00*    (2020.01)
(Continued)

(52) U.S. Cl.
CPC ........ *A61K 41/0061* (2013.01); *A61K 9/0014* (2013.01); *A61K 9/0019* (2013.01);
(Continued)

(58) Field of Classification Search
CPC .......... A61N 2005/0663; A61N 5/0616; A61N 5/062
See application file for complete search history.

(56) References Cited

U.S. PATENT DOCUMENTS

| 2008/0091250 | A1  | 4/2008  | Powell |
| 2009/0247932 | A1  | 10/2009 | Barolet |
| 2010/0137439 | A1* | 6/2010  | Wulf ........................ A61P 17/00 514/561 |

FOREIGN PATENT DOCUMENTS

| CN | 101588792 A | 11/2009 |
| GB | 2 454 652 A | 5/2009 |

(Continued)

OTHER PUBLICATIONS

Novak et al., "Photodynamic Treatment of Actinic Keratosis Using Ameluz® : Recapitulation of Clinical Phase III Studies in the Light of Novel Preclinical Research", New Research, 2013, pp. 93-109. (Year: 2013).*

(Continued)

*Primary Examiner* — Deanna K Hall
(74) *Attorney, Agent, or Firm* — Knobbe, Martens, Olson & Bear, LLP

(57) ABSTRACT

The present invention relates to a composition comprising a photosensitizer use in prevention or treatment of dermatological disease in a patient, wherein the composition is used in the following order of steps:
(a) topical application or subcutaneous injection of said composition to an area of the skin of said patient, (Continued)

Figure 1:
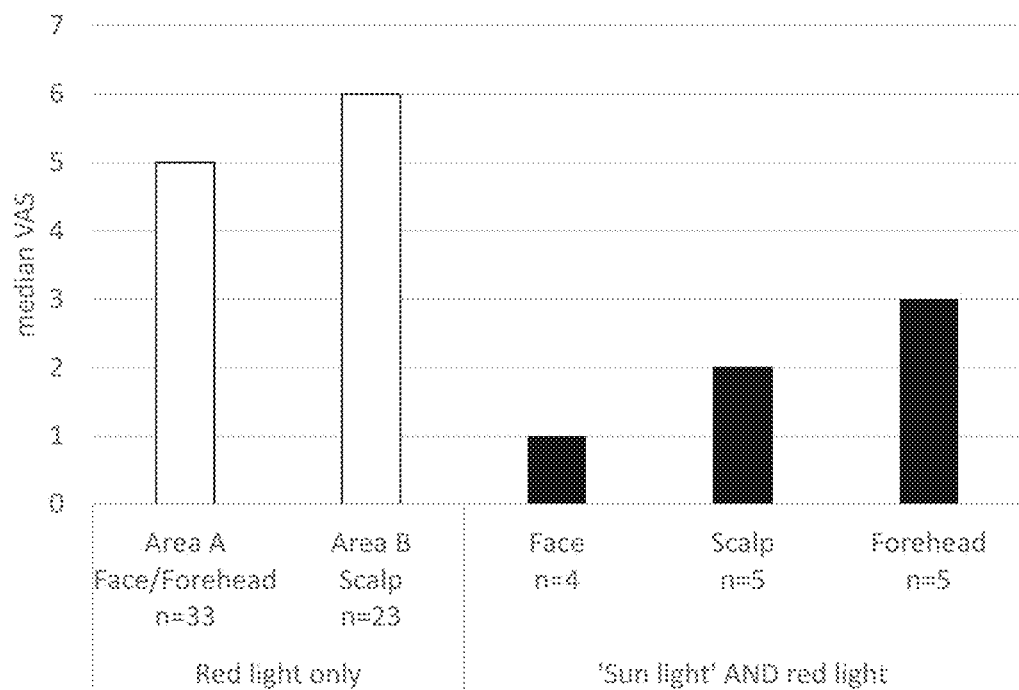

(b) exposure of at least said area of the skin to light with a wavelength spectrum similar or identical to sun light for a duration of 30 min to 5 hours, and (c) exposure of at least said area of the skin to light of a wavelength spectrum comprising only one maximum in the absorbance spectrum of said photosensitizer as well as to methods of treating dermatological disease using the outlined steps and kits of parts comprising such compositions and light sources suitable to apply the respectively indicated light.

20 Claims, 1 Drawing Sheet

(51) Int. Cl.
- A61P 17/02 (2006.01)
- A61K 9/00 (2006.01)
- A61K 9/107 (2006.01)
- A61K 47/10 (2017.01)
- A61K 47/24 (2006.01)

(52) U.S. Cl.
CPC ............ *A61K 9/1075* (2013.01); *A61K 47/10* (2013.01); *A61K 47/24* (2013.01); *A61N 5/062* (2013.01); *A61N 5/0616* (2013.01); *A61P 17/02* (2018.01); *A61N 2005/0663* (2013.01)

(56) References Cited

FOREIGN PATENT DOCUMENTS

| GB | 2454652 | 5/2009 |
| GB | 2454652 A | 5/2009 |
| WO | WO 2014/177837 | 6/2014 |
| WO | WO 2014/177837 A1 | 11/2014 |

OTHER PUBLICATIONS

International Preliminary Report on Patentability dated Feb. 23, 2021 in International Application No. PCT/EP2018/072823, in 10 pages.

Kaneko et al., "Fluorescence-Guided Resection of Malignant Glioma with 4-ALA", International Journal of Biomedical Imaging, Jun. 27, 2016, vol. 2016, Article ID 6135293, 11 pages.

Novak et al., "Photodynamic Treatment of Actinic Keratosis Using Ameluz® : Recapitulation of Clinical Phase III Studies in the Light of Novel Preclinical Research", New Research, 2013, pp. 93-109.

International Search Report dated May 31, 2019 in International Application No. PCT/EP2018/072823, in 5 pages.

Novak et al., "Photodynamic Treatment of Actinic Keratosis using Ameluz: Recapitulation of Clinical Phase III Studies in the light of novel Preclinical Research", *Photodynamic Therapy: New Research*, 2013, pp. 93-109, ISBN: 978-1-62417-635-7.

Reinhold et al., "A randomized, double-blind, phase III, multicentre to evaluate the safety and efficacy BF-200 ALA (Ameluz) vs. placebo in the field-directed treatment of miid-to-moderate actinic keratosis with photodynamic therapy (PDT) when using the BF-RhodoL", *British Journal of Dermatology*, vol. 175, No. 4, Oct. 1, 2016, pp. 696-705.

\* cited by examiner

PHOTODYNAMIC THERAPY COMPRISING TWO LIGHT EXPOSURES AT DIFFERENT WAVELENGTHS

CROSS REFERENCE TO RELATED APPLICATIONS

The present application is a U.S. national phase application under 35 U.S.C. § 371 of International Application No. PCT/EP2018/072823, filed on Aug. 23, 2018 and published as WO 2020/038583 A1 on Feb. 27, 2020, the entire content of which is incorporated herein by reference in its entirety.

The present invention relates to the use of photosensitizers in an improved photodynamic therapy with reduced side effects, in particular pain. In particular the present invention relates to a composition comprising a photosensitizer used in prevention or treatment of dermatological disease in a patient, wherein the composition is used in the following order of steps:
(a) topical application or subcutaneous injection of said composition to an area of the skin of said patient,
(b) exposure of at least said area of the skin to light with a wavelength spectrum similar or identical to sun light for a duration of 30 min to 5 hours, and
(c) exposure of at least said area of the skin to light of a wavelength spectrum comprising only one maximum in the absorbance spectrum of said photosensitizer
as well as to methods of treating dermatological disease using the outlined steps and kits of parts comprising such compositions and light sources suitable to apply the respectively indicated light.

BACKGROUND OF THE INVENTION

Photodynamic therapy (PDT) is a minimally invasive therapeutic modality used for the treatment of various abnormalities or disorders of the skin or other epithelial organs or mucosa, especially cancers or pre-cancerous lesions, as well as certain nonmalignant lesions (e.g. skin complaints such as psoriasis, actinic keratoses (AK) and (acne). PDT involves the application of a photosensitizer systemically or locally to the affected area of the body, followed by exposure to photoactivating light in order to activate the photosensitizer and convert it into a cytotoxic form, whereby the affected cells are killed or their proliferative potential is diminished.

A range of photosensitizers are known in the art, including the psoralens, the porphyrins (e.g. Photofrin®), the chlorins and the phthalocyanins. For topical or subcutaneous application the clinically most relevant photosensitizers today are pre-cursor forms of photosensitizers that are metabolically converted in the target cells. Most relevant are 5-aminolevulinic acid (ALA) and its derivatives, for example esters such as 5-ALA esters.

Although PDT with 5-ALA and 5-ALA derivatives is clinically very effective in the treatment of a wide range of diseases this treatment also results in side-effects. These often include pain, erythema, swelling, edema, burning, itching, exfoliation, hyperpigmentation and prolonged irritation and hypersensitivity after treatment. Such side-effects are particularly undesirable when the treatment site is the face, scalp or neck. This is frequently the case when the PDT is for the treatment of lesions (e.g. actinic keratosis, acne, basal cell carcinoma, warts, psoriasis, rosacea, wound healing, squamous cell carcinoma in situ or other hyperproliferating or infectious disorders) and when PDT is performed using short-term illumination with high-power light sources. In particular the often substantive pain experienced by the patients in these circumstances results in poor acceptance of this treatment, in particular if PDT has to be applied more than once or on extended skin regions.

An alternative treatment is daylight PDT, which uses sun light with increased exposure time to activate the photosensitizer instead of the high-power light sources used in conventional PDT. The side effects of daylight PDT, in particular the pain, are significantly reduced (Dirschka et al., J Eur Acad Dermatol Venereol. 2018 Jul. 19). While the efficacy of daylight PDT seems comparable to conventional PDT, the recurrene rate is significantly higher in daylight PDT.

The present invention teaches the use of photosensitizers in an improved PDT comprising two different light exposures. The present invention therefore provides inter alia the advantages of reduced side effects, in particular reduced pain, and a low recurrence rate.

SUMMARY OF THE INVENTION

In a first aspect, the present invention provides a composition comprising a photosensitizer for use in prevention or treatment of dermatological disease in a patient, wherein the composition is used in the following order of steps:
(a) application of said composition to an area of the skin of said patient,
(b) exposure of at least said area of the skin to light with a wavelength spectrum similar or identical to sun light for a duration of 30 min to 5 hours, preferably 1 to 3 hours, more preferably 1 to 2 hours, and
(c) exposure of at least said area of the skin to light of a narrower wavelength spectrum compared to step (b), preferably comprising only one maximum in the absorbance spectrum of said photosensitizer.

In a second aspect, the present invention provides a method of treating or preventing a dermatological disease in a patient in need thereof in which a photosensitizer is applied to an area of the skin of the patient as indicated in the first aspect of the invention.

In a third aspect, the present invention provides a kit of parts comprising a light source capable of emitting light with a wavelength spectrum and preferably also irradiance similar or identical to sun light and/or yellow-red or violet-blue light and an instruction manual for carrying out steps (b) and (c) of the method of the second aspect of the invention.

In a fourth aspect, the present invention provides a light source capable of emitting light with a wavelength spectrum and preferably also irradiance similar or identical to sun light and yellow-red or violet-blue light and a controller, wherein the controller is programmed for carrying out steps (b) and (c) of the method of the second aspect of the invention.

LIST OF FIGURES in the following, the content of the figures comprised in this specification is described. In this context please also refer to the detailed description of the invention above and/or below.

FIG. 1: Side effect of PDT (pain score) refers to a comparison of the pain experienced by photodynamic therapy using a 5-ALA photosensitizer followed by illumination with a commonly used PDT red light source, as compared to using 5-ALA in combination with the PDT of the present invention using a combination of initially artificial daylight followed by the identical red light illumination. The pain was scored with a visual analog scale for pain (VAS). The area of treatment had an influence on the pain experienced in both treatments. Surprisingly the pain experienced was significantly reduced when using a combination of daylight and red light after application of the photosensitizer as opposed to only red light illumination after application of the photosensitizer.

Figure 2:
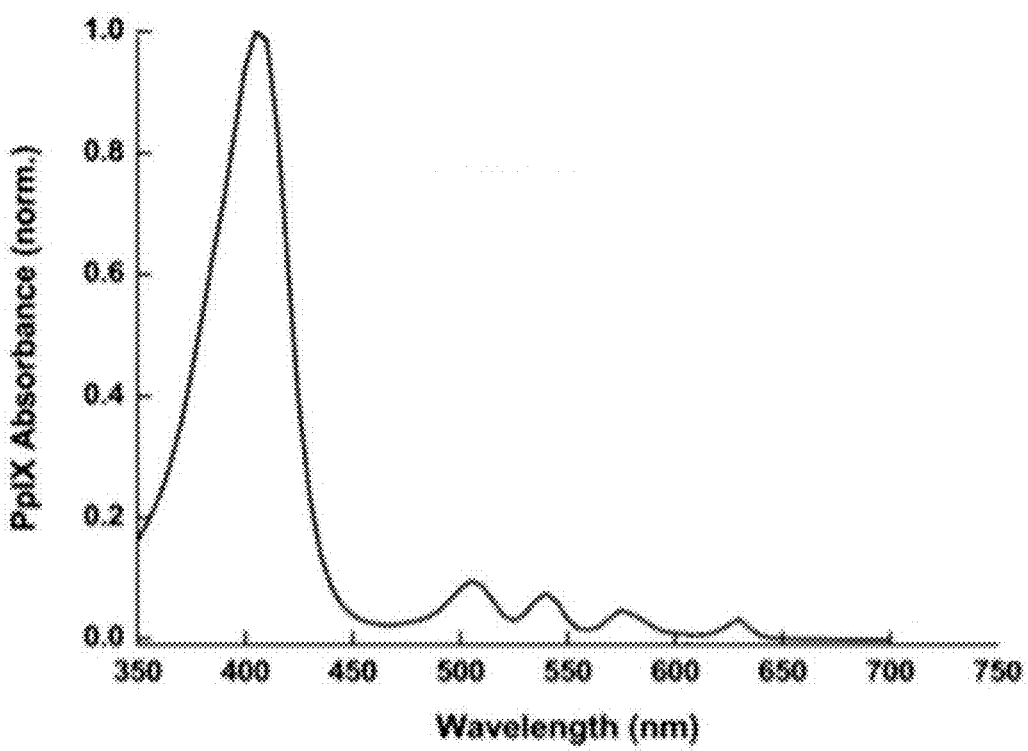

FIG. 2: Absorbance spectrum of protoporphyrin IX (PpIX) refers to the absorbance spectrum in the range of 350 nm to 700 nm. The highest absorption maximum is located at 405 nm. A much smaller but, due to the greatly better tissue penetration of longer-wave light, clinically nevertheless significant absorption maximum is located at 635 nm. In between three additional maxima are located in the range of 500 nm to 550 nm.

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

DEFINITIONS

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The term 'photosensitizer', as used herein, refers to light-sensitive molecules that are activated by the absorption of light. The photoactivation of the photosensitizer can cause the formation of reactive oxygen species (including singlet oxygen) in a photochemical reaction. These reactive oxygen species can destroy the cells that have taken up the photosensitizer. A photosensitizer in the context of the present invention can refer to a direct photosensitizer i.e. a light-sensitive molecule or to a precursor to a direct-photosensitizer that is converted to a direct photosensitizer in the targeted cells. Non-limiting examples of direct photosensitizers are porphyrins (e.g. Photofrin), chlorins and phtalocyanins. Non-limiting examples of a precursor to a photosensitizer are 5-aminolevulinic acid (ALA) and its derivatives, for example esters such as 5-ALA esters. ALA functions as a biosynthetic precursor of the direct photosensitizer protoporphyrin IX (PpIX). All derivatives of ALA suitable for the present invention have in common that they can be metabolized into PpIX.

PpIX exhibits several absorption peaks (see FIG. 2) with the maximum light absorption (the so-called Soret peak) at 405 nm and a much weaker absorption peak at 635 nm. The latter absorption peak can be used to excite PpIX while reducing interference from blood-borne hemoglobin (which has lower absorption at 635 nm). PpIX further has an absorption peak at 505 nm. The absorbance of PpIX in relation to the wavelength ranging from 350 nm to 700 nm is shown exemplary in FIG. 2. While the person skilled in the art is aware that a molecule can be excited with minimal energy at a wavelength identical to the wavelength of the absorption maximum, it is also possible to photoactivate (=excite) a molecule with light of different wavelengths. Use of a wavelength different from the highest absorption maximum can be useful to elicit different effects, such as reduced interference with other light absorbing molecules in the target tissue or higher tissue penetration as is the case with red light as compared to violet-blue light. In the case of PpiX violet (or blue) light most suitable to excite PpIX at 405 nm requires considerable less energy to excite PpIX as compared to red light most suitable to excite PpIX at 635 nm. However, the tissue penetration of red light is much higher than that of violet (or blue) light and red light is therefore more suitable to excite PpIX at deeper levels of the epidermis (Moan et al., Proceedings of the SPIE, 1996, Vol. 2625, p 544-549), particularly where the epidermis displays areas of budding and/or papillary sprouting (Schmitz et al., J Dtsch Dermatol Ges. 2018 August; 16(8):1002-1013).

The term 'wavelength spectrum', as used herein, refers to light of a certain range of wavelengths. For example the wavelength spectrum of red light is 620 nm to 750 nm. A narrower wavelength spectrum comprises a smaller range of wavelengths as the spectrum referred to. For example the wavelength spectrum of red light (620 nm to 750 nm) is a narrower wavelength spectrum as compared to the wavelength spectrum of sun light (about 100 nm to 1000 nm).

The term 'visual analog scale for pain' or 'VAS', as used herein, refers to a unidimensional measure of pain intensity (see McCormack et al. Psychol Med 1988; 18: 1007-19). The pain VAS is a continuous scale comprised of a line, usually 10 centimeters (100 mm) in length, anchored by 2 verbal descriptors, one for each symptom extreme. For pain intensity, the scale was anchored by "no pain" (score of 0) and "pain as bad as it could be" or "worst imaginable pain" (score of 10).

The term 'irradiance', as used herein, refers to the radiant flux (or power) received by a surface per unit area and is expressed as watt per square centimeter ($W/cm^2$). The term 'irradiance' is used equivalently with 'intensity' with regard to light intensities.

The term 'radiant exposure', as used herein, refers to the radiant energy received per unit area (Joule per square centimeter; $J/cm^2$) or in other words the irradiance of a surface integrated overtime of irradiation. The term is used equivalently with the terms 'effective light dose' and 'radiant fluence'.

EMBODIMENTS

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention provides a composition comprising a photosensitizer for use in prevention or treatment of dermatological disease in a patient, wherein the composition is used in the following order of steps:
(a) topical application or subcutaneous injection of said composition to an area of the skin of said patient,
(b) exposure of at least said area of the skin to light with a wavelength spectrum and preferably also irradiance similar or identical to sun light for a duration of 30 min to 5 hours, preferably 1 to 3 hours, more preferably 1 to 2 hours, and
(c) exposure of at least said area of the skin to light of a narrower wavelength spectrum compared to step (b), preferably comprising only one maximum in the absorbance spectrum of said photosensitizer, more preferably comprising the maximum at 635 nm.

An absorbance spectrum is a plot of absorbance as a function of wavelength. The skilled person is aware of various methods to measure the absorbance spectrum of a compound. One such method is spectrophotometry. Therefore, a spectrophotometer transmits light of narrow wavelength ranges, typically 0.1 nm, 0.5 nm or 1 nm, through a sample comprising the compound to be tested in solution. The spectrophotometer measures the light absorbed by the compound. Using such a measurement over a certain range of wavelengths, such as visible light for example, generates an absorbance spectrum of said compound. The curve representing such an absorbance spectrum usually has one or more maxima with an absorption peak. The peak of a maximum is referred to as an absorption peak. The skilled person is further aware how to define the maxima of a curve such as an absorbance spectrum by mathematical means known in the art. One such method for a curve that can be differentiated is a derivative test. This test can distinguish between a maximum, a minimum and a saddle point of a curve. In a first derivative test the slope of a curve is identified. A maximum in a curve is a point where the curve switches from increasing to decreasing in that point. In other word the first derivative of a curve is 0 at a maximum. In a second derivative test it is determined if the point identified in the first derivate test is a maximum. In the case the second derivative in this point is less than 0 the curve has a maximum at this point.

In other words the area to be treated is, after application of the composition comprising the photosensitizer, exposed to light with a wavelength spectrum similar or identical to sun light for a duration of at least 30 minutes, followed by exposure to light with a narrower wavelength spectrum. The wavelength spectrum of the second exposure comprises the wavelength of only one maximum of the absorbance spectrum (=absorption peak) of said photosensitizer.

In a preferred embodiment of the first aspect of the present invention, the light of step (c) is red light, blue light, green light or violet light.

Red light refers to light with a wavelength spectrum of 620 nm to 750 nm. Violet light refers to light with a wavelength spectrum of 380 nm to 450 nm. Blue light refers to light of a wavelength spectrum of 450 nm to 495 nm. Green light refers to light with a wavelength spectrum of 495 nm to 570 mn.

In a preferred embodiment of the first aspect of the present invention, the light of step (c) is red light or violet light. Red light refers to light with a wavelength spectrum of 620 nm to 750 nm. Violet light refers to light with a wavelength spectrum of 380 nm to 450 nm.

In a preferred embodiment of the first aspect of the present invention, the light of step (c) is red light. Red light has the particular advantage of a superior tissue penetration as compared to light with shorter wavelengths.

In a preferred embodiment of the first aspect of the present invention, the area of the skin comprises skin effected by the disease or skin prone to be effected by the disease.

In a preferred embodiment of the first aspect of the present invention, there is a residence time interval subsequent to step (a) and prior to step (b) of 1 to 90 min, in particular of 5 to 60 min, more particular of 15 to 30 min, preferably in the absence of light exposure. The residence time interval allows time for the composition or at least the photosensitizer comprised within to reach the intended target cells/tissue. A residence time is particularly useful if the photosensitizer used is a precursor to the actual photosensitizer to allow for the metabolic conversion and accumulation of the actual photosensitizer resulting from the precursor. The residence time can be in the absence of light exposure. This is particularly useful to avoid photobleaching of the photosensitizer, which can occur after exposure to light.

In a preferred embodiment of the first aspect of the present invention, the light used in step (b) has an irradiance and/or spectral distribution that is similar to that of average sun light. Step (b) is preferably carried out when the patient is positioned in locations where the patient can stay pleasantly, depending on the weather either outside in the shade or the sun or inside adjacent to a window.

In a preferred embodiment of the first aspect of the present invention, the light used in step (b) is a synthetic light with a wavelength spectrum similar or identical to sun light (=daylight).

In a preferred embodiment of the first aspect of the present invention, the light used in step (b) results in a radiant exposure of at least 8 J/cm$^2$, preferably of 8-75 J/cm$^2$, more preferably 10-40 J/cm$^2$, most preferably of 15-30 J/cm$^2$.

In a preferred embodiment of the first aspect of the present invention, the light used in step (b) has a lower irradiance than the light used in step (c), preferably the irradiance is between 2- and 15-times lower than that in step (c), i.e. 2-, 3-, 4-, 5-, 6-, 7-, 8-, 9-, 10-, 11-, 12-, 13- 14- or 15-times lower.

In a preferred embodiment of the first aspect of the present invention, step (b) is performed at a temperature of at least 10° C., preferably at least 15° C., more preferably at least 20° C. The temperature is important with regard of the skin temperature of the subject the composition is applied to. The lower the skin temperature is, the slower does uptake or metabolic conversion in case of a precursor of the photosensitizer take. If the temperature is too low the amount of photosensitizer in the target cells can be insufficient to affect the target cells.

In a preferred embodiment of the first aspect of the present invention, the light of step (b) has a wavelength spectrum of visible light (i.e. 380 nm to 780 nm), preferably with equal irradiance throughout or irradiance peak(s) at around 410 and/or 505 and/or 635 nm.

In a preferred embodiment of the first aspect of the present invention, the light of step (b) has a wavelength spectrum of 570 nm to 650 nm, preferably 570 nm to 630 nm.

In a preferred embodiment of the first aspect of the present invention, the light of step (b) has a wavelength spectrum of 360 nm to 460 nm, preferably 380 nm to 440 nm.

In a preferred embodiment of the first aspect of the present invention, the light of step (b) is yellow and/or orange light. Yellow light refers to light with a wavelength spectrum of 570 nm to 590 nm. Orange light refers to light with a wavelength spectrum of 590 nm to 620 nm.

In a preferred embodiment of the first aspect of the present invention, the light of step (c) has a wavelength in the range of 570 nm to 750 nm, preferably of 570 nm to 670 nm, more preferably of about 635 nm.

In a preferred embodiment of the first aspect of the present invention, the light of step (c) has a wavelength in the range of 360 nm to 495 nm, preferably 360 nm to 460 nm, more preferably of about 410 nm.

In a preferred embodiment of the first aspect of the present invention, the red light of step (c) results in a radiant exposure of 10-75 J/cm$^2$, preferably of 25-75 J/cm$^2$, more preferrably about of 25-45 J/cm$^2$, most preferably about 37 J/cm$^2$.

In a preferred embodiment of the first aspect of the present invention, the violet light of step (c) results in a radiant exposure of 1-30 J/cm$^2$, preferably 5-15 J/cm$^2$.

In a preferred embodiment of the first aspect of the present invention, the exposure of step (c) has a duration of at least 5 minutes, preferably of 5-60 minutes, more preferably 5-30 minutes, most preferably 5-20 minutes.

In a preferred embodiment of the first aspect of the present invention, the photosensitizer is selected from 5-aminolevulinic acid (ALA). ALA-esters, in particular methyl-5-amino-4-oxopentanoat, or hexyl-5-amino-4-oxopentanoat or their derivatives. In the context of the present invention precursors, in particular biosynthetic precursors, are also referred to as photosensitizer. For example 5-aminolevulinic acid (ALA) and its derivatives are biosynthetic precursors. Only after metabolic conversion of ALA the light sensitive molecule protoporphyrin IX is synthesized, which mediates the effect of PDT in response to photoactivation.

In a preferred embodiment of the first aspect of the present invention, the composition is formulated as a nanoemulsion additionally comprising:
  (a) at least one aqueous component, and
  (b) a carrier, which comprises:
    (i) at least one lipophilic component,
    (ii) at least one surfactant and
    (iii) at least one alcohol.

The photosensitizer has to be taken up by the target cell to be effective or in case of the photosensitizer being a precursor to be converted first. The formulation of the composition as a nanoemulsion facilitates the uptake of the photosensitizer.

In a preferred embodiment of the first aspect of the present invention, the carrier is present in the aqueous component and the surfactant is present in an amount of from 1% by weight to 30% by weight and the alcohol is present in an amount of from 0.1% by weight to 10% by weight, based on the total weight of the nanoemulsion.

In a preferred embodiment of the first aspect of the present invention, the carrier is present in the aqueous component.

In a preferred embodiment of the first aspect of the present invention, the surfactant is present in an amount of from 1% by weight to 30% by weight and the alcohol is present in an amount of from 0.1% by weight to 10% by weight, based on the total weight of the nanoemulsion.

In a preferred embodiment of the first aspect of the present invention, the aqueous component is present in an amount of from 50% by weight to 98% by weight, based on the total weight of the nanoemulsion.

In a preferred embodiment of the first aspect of the present invention, the at least one alcohol is isopropylalcohol and/or 1-propylalcohol.

In a preferred embodiment of the first aspect of the present invention, the at least one lipophilic component are triglycerides and/or a mixture thereof.

In a preferred embodiment of the first aspect of the present invention, the at least one surfactant is lecithin and/or a polyoxyethylene-type surfactant.

In a preferred embodiment of the first aspect of the present invention, the mean diameter of the emulsified particles ranges from 10 to 100 nm.

In a preferred embodiment of the first aspect of the present invention, the dermatological disease is a hyperproliferative disease, preferably keratosis, more preferably actinic keratosis; basal carcinoma, squamous cell carcinoma in situ, warts, acne, rosacea or an inflammatory or infectious dermatological condition.

In a second aspect, the present invention provides a method of treating or preventing a dermatological disease in a patient in need thereof in which a photosensitizer is applied to an area of the skin of the patient as indicated in the first aspect of the invention. Accordingly, the method of the present invention provides a method of treating or preventing a dermatological disease in a patient in need thereof comprising the steps:
(a) topical application or subcutaneous injection of said composition to an area of the skin of said patient,
(b) exposure of at least said area of the skin to light with a wavelength spectrum similar or identical to sun light for a duration of 30 min to 5 hours, preferably 1 to 3 hours, more preferably 1 to 2 hours, and
(c) exposure of at least said area of the skin to light of a narrower wavelength spectrum compared to step (b), preferably comprising only one maximum in the absorbance spectrum of said photosensitizer, more preferably comprising the maximum at 635 nm.

All of the above indicated preferred embodiments of the first aspect of the invention are similarly preferred in the context of the method of the invention.

In a third aspect, the present invention provides a kit of parts comprising a light source capable of emitting light with a wavelength spectrum similar or identical to sun light and/or yellow-red or violet-blue light and an instruction manual for carrying out steps (b) and (c) of the method of the second aspect of the invention.

In a fourth aspect, the present invention provides a light source capable of emitting light with a wavelength spectrum and/or irradiance similar or identical to sun light and yellow-red or violet-blue light and a controller, wherein the controller is programmed for carrying out steps (b) and (c) of the method of the second aspect of the invention.

Light sources suitable to be used to emit the light spectrum of step (b) and (c) are individually well known in the art and can be combined to be used in all aspects of the invention.

EXAMPLES

Example 1: Effect of Combined PDT on Pain Experienced

Patients suffering from actininc keratosis (AK) of mild to moderate severity on the face, scalp and/or forehead were treated with BF-200 ALA (Ameluz), which is a topically applied nanoemulsion-based gel containing 7.8% 5-aminolevulinic acid (ALA). The application was followed by a residence time in the absence of light, followed by two different light exposures. The pain experienced by the subjects was determined afterwards by VAS score.

Study Population:

Male and female study subjects (63-85 years of age) diagnosed with clinically confirmed actininc keratosis lesions of mild to moderate intensity were enrolled (see table 1).

TABLE 1

Study population and VAS score

| patient | age | gender | treatment area | cancerized field | clinical grade of AK | VAS | median VAS |
|---|---|---|---|---|---|---|---|
| 1 | 63 | male | face | yes | I-III | 1 | 1 |
| 2 | 70 | male | face | yes | I-III | 0 | |
| 3 | 74 | male | face | yes | I-III | 2 | |
| 4 | 85 | male | face | yes | I-III | 1 | |
| 5 | 79 | male | scalp | yes | I-III | 4 | 2 |
| 6 | 74 | female | scalp | yes | I-III | 2 | |
| 7 | 65 | male | scalp | yes | I-III | 0 | |
| 8 | 76 | male | scalp | yes | I-III | 2 | |
| 9 | 74 | male | scalp | yes | I-III | 4 | |
| 10 | 63 | male | forehead | yes | I-III | 7 | 3 |
| 11 | 65 | female | forehead | yes | I-III | 8 | |
| 12 | 78 | male | forehead | yes | I-III | 2 | |
| 13 | 81 | male | forehead | yes | I-III | 1 | |
| 14 | 75 | male | forehead | yes | I-III | 3 | |
| Overall/median | 74 | | | | | | 2 |

Treatment Protocol:

The study treatment included one single photodynamic therapy (PDT) consisting of one (conventional PDT) or two illumination periods (combined PDT), depending on the study group.

After degreasing and carefully removing scabs, crusts, and hyperkeratoses of AK lesions in the treatment areas, a thin layer of Ameluz was administered to the lesions such that AK lesions and surrounding 0.5-1.0 cm of healthy skin were covered. The treated areas were covered with a light-tight occlusive dressing for 30 minutes. Ameluz remained on the lesions throughout the entire illumination period. Daylight illumination with artificial sun light was performed with an Indoorlux® system (Swiss Red AG; Switzerland) and ranged from 15,000-25,000 Lux, depending on the distance from the light sources (110-150 cm) as described in Kellner et al. (Br J Dermatol. 2015 April; 172(4):1146-8). The irradiances in the spectral areas relevant for the activation of PpIX (green/yellow at 570-590 nm and orange/red at 620-640 nm) were 21.14 and 3.04 mW/cm$^2$, respectively. The combined effective light dose at these wave lengths was 14.3-24.2 J/cm$^2$ depending on the distance from the light sources and, to a lesser extent, from the angle of the treated surface relative to the ceiling, but never below the 9.4-10.8 J/cm$^2$ required for natural daylight PDT. Daylight illumination started immediately following the residence time and removal of the light-tight dressing and lasted for 2 continuous hours.

Then immediately following, the entire treatment field was illuminated using a red light source (BF-RhodoLED lamp) for 10 min at a distance of 5-8 cm from the skin surface, resulting in a total light dose of 37 J/cm$^2$. Immediately after the second light exposure period the experienced pain was assessed using a visual analog scale (VAS)

for pain (see FIG. 1). The results of this study group was compared to a second study group group being part of a phase III trial with BF-200 ALA (Ameluz) as described in Reinhold et al. (Br J Dermatol. 2016 October; 175(4):696-705). Briefly, the second study group also received treatment with BF-200 ALA (Ameluz) as described above with the main difference being that no daylight illumination step was performed (conventional PDT).

The VAS score in the combined PDT group was dependent on the area treated, with the forehead being the area with the most pain experienced (median VAS score 3), followed by the scalp area (median VAS 2) and the face area (median VAS 1). As can be appreciated from FIG. 1, in the conventional PDT group the median VAS score experienced in the face/forehead group (area A) was 5 and in the scalp area (area B) a median VAS score of 6 was determined. This results in a significant reduction of pain in the combined PDT group as compared to conventional PDT.

Example 2: Efficiency of Combined PDT in the Treatment of Actininc Keratosis

The efficiency of conventional PDT and combined PDT as described in example 1 with regard to clearance of individual lesions was assessed by visual inspection and by palpation and compared with baseline at 12 weeks after treatments.

Both PDT treatments used (see example 1) resulted in a complete clearance rate of lesions above 90%. The cosmetic outcome with regard to skin quality was also not significantly different from the results achieved with conventional PDT.

Example 3: Recurrence Rate of Combined PDT

The recurrence rate of actininc keratosis after 12 months post treatment is significantly different in conventional PDT as compared with daylight PDT. In conventional PDT the recurrence rate for mild lesions is 5.2% as compared to 17.7% for daylight PDT and for moderate lesions 11.4% and 20.1%, respectively. This results in an overall 12 months post treatment recurrence rate of 9.4% for conventional PDT as compared to 19.9% for daylight PDT. This significant difference in recurrence rate represents the major disadvantage of daylight PDT.

At the day of application the 12-month post treatment period has not been reached for the whole study population, but initial results show an overall 12-month post treatment recurrence rate of about 10% in the combined PDT group. This is virtually identical to the 9.4% recurrence rate achieved for conventional PDT and significantly improved from the 19.9% achieved with daylight PDT alone.

In summary, the present invention teaches a new application regime for photosensitizers in photodynamic therapy (PDT) surprisingly combining the advantages of daylight PDT, with regard to a significant reduction in pain, and the advantages of conventional PDT, with regard to the lower recurrence rates.

The invention claimed is:

1. A method of preventing or treating a dermatological disease in a patient, the method comprises the following order of steps:
   (a) topical application or subcutaneous injection of a composition comprising a photosensitizer to an area of the skin of said patient,
   (b) exposure of at least said area of the skin to light with a wavelength spectrum and preferably also irradiance similar or identical to sun light for a duration of 30 min to 5 hours, preferably 1 to 3 hours, more preferably 1 to 2 hours, and
   (c) exposure of at least said area of the skin to light of a narrower wavelength spectrum compared to step (b), preferably comprising only one maximum in the absorbance spectrum of said photosensitizer.

2. The method of claim 1, wherein the composition is formulated as a nanoemulsion additionally comprising:
   (a) at least one aqueous component, and
   (b) a carrier, which comprises:
      (i) at least one lipophilic component,
      (ii) at least one surfactant and
      (iii) at least one alcohol.

3. The method of claim 2, wherein
   the carrier is present in the aqueous component and/or
   the surfactant is present in an amount of from 1% by weight to 30% by weight and the alcohol is present in an amount of from 0.1% by weight to 10% by weight, based on the total weight of the nanoemulsion.

4. The method of claim 2, wherein the aqueous component is present in an amount of from 50% by weight to 98% by weight, based on the total weight of the nanoemulsion.

5. The method of claim 2, wherein:
   the at least one alcohol is isopropylalcohol and/or 1-propylalcohol and/or
   the at least one lipophilic component are triglycerides and/or a mixture thereof and/or
   the at least one surfactant is lecithin and/or a polyoxyethylene-type surfactant and/or
   the mean diameter of particles of the nanoemulsion ranges from 10 to 100 nm.

6. The method of claim 2, wherein the photosensitizer is selected from 5-aminolevulinic acid (ALA), ALA-esters, in particular methyl-5-amino-4-oxopentanoat, or hexyl-5-amino-4-oxopentanoat or their derivatives.

7. The method of claim 1, wherein the light used in step (c) is red light or violet light.

8. The method of claim 1, wherein the area of the skin comprises skin effected by the disease or skin prone to be affected by the disease.

9. The method of claim 1, wherein there is a residence time interval subsequent to step (a) and prior to step (b) of 1 to 90 min, in particular of 15 to 30 min, preferably in the absence of light exposure.

10. The method of claim 1, wherein the light used in step (b) has an irradiance that is similar to that of average sunlight, preferably in locations where the patient can stay pleasantly, depending on the weather either in the shade or the sun.

11. The method of claim 1, wherein the light of step (b) has a wavelength spectrum of 380 nm to 780 nm, preferably with equal irradiance throughout or irradiance peak(s) at around 405 and/or 505 and/or 635 nm.

12. The method of claim 1, wherein:
   the light of step (c) has a wavelength in the range of 570 nm to 750 nm, preferably of 570 nm to 670 nm, more preferably of about 635 nm; or
   the light of step (c) has a wavelength in the range of 360 nm to 495 nm, preferably 360 nm to 460 nm, more preferably of about 410 nm.

13. The method of claim 7, wherein:
   the red light of step (c) results in a radiant exposure of 10-75 $J/cm^2$, preferably of 25-45 $J/cm^2$; or
   the violet light of step (c) results in a radiant exposure of 1-30 $J/cm^2$, preferably 5 to 15 $J/cm^2$.

14. The method of claim 1, wherein the light used in step (b) has a lower irradiance than the light used in step (c), preferably the irradiance is 2- to 15-times lower than step (c).

15. The method of claim 1, wherein the exposure of step (c) has a duration of at least 5 minutes, preferably of 5-60 minutes, more preferably 10-30 minutes.

16. The method of claim 1, wherein the dermatological disease is a hyperproliferative disease, preferably keratosis, more preferably actinic keratosis; basal carcinoma, squamous cell carcinoma in situ, warts, acne, rosacea or an inflammatory or infectious dermatological condition.

17. A method of treating or preventing a dermatological disease in a patient in need thereof comprising:
(a) topical application or subcutaneous injection of a composition comprising a photosensitizer to an area of the skin of said patient,
(b) exposure of at least said area of the skin to light with a wavelength spectrum similar or identical to sun light for a duration of 30 min to 5 hours, preferably 1 to 3 hours, more preferably 1 to 2 hours, and
(c) exposure of at least said area of the skin to light of a narrower wavelength spectrum compared to step (b), preferably comprising only one maximum in the absorbance spectrum of said photosensitizer, more preferably comprising the maximum at 635 nm.

18. The method of claim 17, wherein the composition is formulated as a nanoemulsion additionally comprising:
(a) at least one aqueous component, and
(b) a carrier, which comprises:
(i) at least one lipophilic component,
(ii) at least one surfactant and
(iii) at least one alcohol.

19. A kit comprising a light source capable of emitting light with a wavelength spectrum and preferably also irradiance similar or identical to sun light and/or yellow-red or violet-blue light and an instruction manual for carrying out steps (b) and (c) of the method of claim 17.

20. A light source capable of emitting light with a wavelength spectrum and preferably also irradiance similar or identical to sun light and yellow-red or violet-blue light and a controller, wherein the controller is programmed for carrying out steps (b) and (c) of the method of claim 17.

* * * * *